United States Patent [19]

Rutanen

[11] Patent Number: 5,554,504
[45] Date of Patent: Sep. 10, 1996

[54] DIAGNOSTIC METHOD FOR DETECTING THE RUPTURE OF FETAL MEMBRANES

[75] Inventor: Eeva-Marja Rutanen, Espoo, Finland

[73] Assignee: OY Medix Biochemica AB, Kauniainen, Finland

[21] Appl. No.: 81,286

[22] PCT Filed: Dec. 30, 1991

[86] PCT No.: PCT/FI91/00413

§ 371 Date: Jun. 30, 1993

§ 102(e) Date: Jun. 30, 1993

[87] PCT Pub. No.: WO92/12426

PCT Pub. Date: Jul. 23, 1992

[30] Foreign Application Priority Data

Dec. 31, 1990 [FI] Finland .................. 906469

[51] Int. Cl.$^6$ .............. G01N 33/53; G01N 33/543; G01N 33/577

[52] U.S. Cl. ........... 435/7.8; 435/7.9; 435/7.92; 435/7.94; 436/510; 436/518; 436/548; 436/65; 436/87; 436/814

[58] Field of Search .................. 436/548, 524, 436/533, 530, 534, 811, 510, 65, 814, 87, 518; 435/7.94, 7.92, 7.6, 7.71, 970, 975, 7.8, 7.9; 530/388.1

[56] References Cited

U.S. PATENT DOCUMENTS

| 4,952,517 | 8/1990 | Bahar ........................ 436/518 |
| 5,037,735 | 8/1991 | Khanna et al. ............... 435/7.6 |
| 5,096,830 | 3/1992 | Senyci et al. ................ 436/65 |
| 5,252,459 | 10/1993 | Torcha et al. ................ 435/6 |

FOREIGN PATENT DOCUMENTS

| 0316919 | 11/1988 | European Pat. Off. . |
| 84863 | 10/1991 | Finland . |
| 89/09268 | 5/1989 | WIPO . |
| 90/00569 | 1/1990 | WIPO . |

OTHER PUBLICATIONS

Pekonen, F. et al. A monoclonal antibody-based immuno-radio-metric assay for Ion molecular-weight insulin-like growth factor binding protein/placental protein 12. Journal of Immunoassay 10(4) 325–337, 1989.

Rutanen, E-M, et al. Diagnosis of premature rupture of fetal membranes by the measurement of insulin-like growth factor binding protein-1 in cervical secretion. American Journal of Obstetrics and Gynecology 164(1) 258, Abstract #38, 1991.

Voller, A. Heterogeneous Enzyme-immunoassays and their applications. In: Enzyme-Immunoassay (E. T. Maggio, ed.) Boca Raton, FL: CRC Press, 1987, Ch 9, pp. 181–196.

Oy Medix Biochemica AB. Monoclonal Antibody Catalog, published 1988 as disclosed by Applicant, p. 7 of Paper No. 8 (filed May 26, 1994). pp. 15–16.

Rutanen et al. (1982) *Am. J. Obst. & Gynec.* 144(4): 460–463.

Koistinen et al. (1986) *Endocrinology* 118(4): 1375–1378.

Friedman et al. (1969) *Am. J. Obst. & Gynec.* 104(4):544–550.

Rutanen et al. (1988) *Biochemical & Biophysical Res. Communications* 152(1):208–215.

Rutanen et al. (1985) *Endocrinology* 116(4): 1304–1309.

Povoa et al. (1984) *Acta Endocrinologica* 107:563–570.

Rochelson et al. (1983) *Obstetrics & Gynecology* 62(4): 414–418.

Konickx et al. (1981) *British Journal of Obstetrics & Gynaecology* 88:607–610.

Lee et al. (1988) *Molecular Endocrinology* 2(5): 404–411.

"BR J. Obstet Gynaecol" Rutanen EM—Dec. 1984 pp. 1240–1244, Abstract.

"Clin Chim Acta" Koistinen et al, 1987, 164(3) pp. 293–303, Abstract.

*Primary Examiner*—Christina Y. Chan
*Assistant Examiner*—James L. Grun
*Attorney, Agent, or Firm*—Birch, Stewart, Kolasch & Birch, LLP

[57] ABSTRACT

A rapid diagnostic method for detecting the rupture of fetal membranes is disclosed. The presence of insulin-like growth factor binding protein 1 (IGFBP-1) in a vaginal secretion sample, resulting from the rupture of fetal membranes, is detected with the aid of at least one specific binding substance for IGFBP-1.

11 Claims, No Drawings

DIAGNOSTIC METHOD FOR DETECTING THE RUPTURE OF FETAL MEMBRANES

This application is a 37/of PCT/FI91/00413 filed Dec. 30, 1991.

The present invention relates to a diagnostic method for detecting the rupture of fetal membranes, said method being based on the determination of a protein present in a vaginal secretion sample of a pregnant woman, and a test kit for the diagnosis of the rupture of fetal membranes.

The term "premature rupture of fetal membranes" (PROM) refers to the spontaneous rupture of the membranes at least 24 hours before the onset of labor at term or preterm. It occurs in about 5–10% of deliveries and is the cause of about 10% of perinatal deaths. About 30–50% of the premature ruptures of membranes occur when the gestational age is less than 37 weeks, and thus is not fullterm. In this case the diagnosis is extremely important because the rupture of membranes is associated with a significantly increased risk of an intrauterine infection. The risk of an infection is greater the longer time has elapsed between the rupture of membranes and the delivery. Infections increase both maternal and perinatal mortality.

In spite of the problem being so common and severe, no absolute diagnostic method has been known for detecting the rupture of membranes in cases when the rupture is not clinically evident.

Because of the lack of a definitive method, several unsatisfactory methods have been used when trying to determine the presence of amniotic fluid in the vagina. Known methods are described by, inter alia, Friedman, M. L. and McElin, T. W., Diagnosis of ruptured fetal membranes. *Am. J. Obstet. Gynec.* 1969; 104: 544–550. The amniotic fluid crystallization test is based on observing a characteristic arborization or "fern" pattern on a slide, which pattern differs from that of normal vaginal secretions.

In the dye tests, an attempt is made to detect the difference by dyeing the secretion on a slide with, e.g., Nile Blue, Acridin Orange or Bromthymol Blue. An altered pH in the vaginal secretion can be detected by a Nitrazin test. In the above mentioned article a method is also described wherein amniotic fluid is dyed with a fluorescent compound and its leakage is visually observed in UV light.

These methods are not satisfactory because false positive or false negative results are too often obtained, Or they are sensitive to interfering substances or are associated with a risk to patient health. The test result can be erroneous if there is a vaginal infection, or if a long time has elapsed since the rupture of membranes.

It has also been suggested that, in order to detect premature rupture of fetal membranes,i it could be useful to determine such a compound in the vaginal fluid the concentration of which is high in amniotic fluid compared to the concentration of said compound in those other secretions that could possibly be present in the vagina. Compounds like this have been described: Alpha-fetoprotein (AFP) (Rochelson et al., Rapid assay—possible application in the diagnosis of premature rupture of the membranes. *Obstet Gynecol.* 1983; 62: 414–418) and prolactin (PRL) (Koninckx et al., Prolactin concentration in vaginal fluid: a new method for diagnosing ruptured membranes. *Br. J. Obstet. Gynecol.* 1981; 88: 607–610). The concentration of both compounds in amniotic fluid is clearly higher than in the blood of a pregnant person. However, in a situation where the vaginal fluid sample contains blood, it is difficult to detect the presence of a small amount of amniotic fluid by determining these compounds.

Consequently, it is evident that there is a need for developing a simple and reliable diagnostic method for detecting the rupture of fetal membranes. In the situation when the test is performed, it is extremely important to obtain the test result rapidly. The ideal test for this purpose is simple to perform and rapid (result obtained within at least 30 minutes), and can preferably be performed as a bed-side test immediately on site.

An object of the present invention is thus to provide a new and improved method for detecting the rupture of fetal membranes, the method being specific to the substance to be measured independently of individual variations in patients.

An object of the invention is also to provide a method that is rapid and simple to perform while the patient is waiting (a so-called bed-side test).

An object of the invention is also to develop a test kit suitable for such a diagnosis which kit contains the means for performing a simple and rapid diagnosis method.

The exact features of the invention will become evident from the following description and the appended claims, the content of which is enclosed herein by reference. Thus, the present invention is directed to a diagnostic method for detecting the rupture of fetal membranes, which method is based on the determination of a protein in a vaginal secretion sample of a pregnant woman. Said method is characterized in that the protein to be detected is Insulin-like Growth Factor Binding Protein 1 (IGFBP-1), the presence of which, resulting from the rupture of fetal membranes, is indicated in the sample with the aid of at least one specific IGFBP-1 binding substance.

In the method according it the invention, the ratio of the amount of the specific binding substance to the amount of the protein to be determined is so adjusted that a low concentration of IGFBP-1 does not cause a reaction that is interpreted as being positive. A positive reaction will not be caused by any but a concentration which is so high as to be characteristic only for amniotic fluid. According to the invention, this decreasing of the sensitivity is achieved, for example, by diluting the vaginal sample before performing the test.

The test kit according to the invention developed for the diagnosis of the rupture of fetal membranes is characterized in that it includes at least one reagent which comprises a substance having specific binding activity to Insulin-like Growth Factor Binding Protein 1 (IGFBP-1) for detecting the presence of IGFBP-1 caused by the rupture of fetal membranes in a vaginal secretion sample.

The test kit according to the present invention also preferably contains a label for indicating the binding reaction between IGFBP-1 and the binding substance, and preferably, the specific IGFBP-1 binding substance included in the reagent is a specific antibody to IGFBP-1, particularly a monoclonal antibody.

Insulin-like Growth Factor Binding Protein 1 (IGFBP-1) is a protein that is present in varying concentrations in various male and female body fluids and, e.g., in the serum of a pregnant woman. So far, it has been shown to be synthesized only by liver, predecidualized and decidualized endometrium, as well as ovaries.

IGFBP-1 was first purified from placenta and fetal membranes in 1980 (Bohn et al., Isolierung und Characterisierung eines Neuen Plazentaspezifischen Proteins (PP12), *Arch. gynecol.* 1980; 229: 279–291). It was thought to be a protein of placental origin, and it was called Placental Protein 12 (PP12). Later it was observed that PP12 and IGFBP-1 purified from amniotic fluid have the same N-terminal amino acid sequence (Povoa et al., Cross-reactions of serum somatomedin-binding protein in a radioimmunoassay developed for somatomedin-binding protein isolated from human amniotic fluid. *Acta Endocrinologica* 1984; 107: 563–570) and that PP12 binds IGF I (Insulin-like Growth Factor I) (Koistinen et al., Placental protein 12 is a decidual protein that binds somatomedin and has an identical N-terminal amino acid sequence with somatomedin-binding protein from human amniotic fluid *Endocrinology* 1986; 118: 1375). Synthesis of IGFBP-1 in decidua was first described in 1985 (Rutanen et al., Synthesis of placental protein 12 by human decidua. *Endocrinology* 1985; 116: 1304). Purification of IGFBP-1 from a human hepatoma cell line was published in 1988 (Lee et al., Insulin-like growth factor (IGF) binding protein complementary deoxyribonucleic acid from human HEP G2 hepatoma cells, *Moll. Endocrinol.* 1988; 2: 404). It was in this connection that the complete amino acid sequence of the protein was reported for the first time.

The concentration of IGFBP-1 in amniotic fluid has been observed to be usually 100 to 1000 times higher than that in maternal serum (Rutanen et al., Radioimmunoassay of placental protein 12: levels in amniotic fluid, cord blood and serum of healthy adults, pregnant women and patients with trophoblastic disease. *Am. J. Obstet. Gynecol.* 1982; 144: 460). However, clinical applications to this observation have not been described so far.

Reactions based on specific binding substances are generally known. Antibodies are the compounds most commonly used as specific binding substances. These so-called immunological methods are based on the ability of an antibody to bind specifically to a certain site in its antigen (epitope). The so-called polyclonal antibodies are a mixture of immunoglobulins in serum of an immunized animal. The mixtures are different in each individual animal. Unlike this, the so-called monoclonal antibodies are produced by one cell line that is cultured under laboratory conditions, and each antibody is homogenous and can be characterized by methods used in protein chemistry and continuously produced in identical form.

An immunological method can be developed so that only one antibody is used. In this case, the reaction conditions are chosen so as to allow the antigen in the sample to compete with an added antigen that is labelled, but otherwise identical to the sample antigen, for a limited amount of binding sites in the antibody. The concentration of the sample antigen is determined by analyzing the fraction of bound label. Several labelling substances that produce a signal enabling measurement of concentration may be used, e.g., radioactive isotopes, enzymes, chemiluminescent or fluorescent compounds. The method may also employ two different antibodies (the so-called sandwich principle). Here, the antibodies are specific to separate epitomes in the same antigen, and can bind simultaneously to the same antigen molecule. One antibody is usually immobilized on a solid carrier and the other is labelled. Both antibodies bind to the antigen in the sample, and the complex can be separated from unbound label with the aid of the carrier. The amount of bound labelled antibody is directly proportional to the antigen concentration in the sample.

The inventor of the present invention has studied placental proteins, and for her research work she has developed a radioimmunoiogical assay method for determining IGFBP-1 (PP12) concentration. Moreover, monoclonal antibodies to IGFBP-1 have been developed for the studies (Rutanen et al., Monoclonal antibodies to the 27–34K insulin-like growth factor binding protein. *Biochem. Biophys. Res. Commun.* 1988; 152: 208). The studies have not, however, led to any clinical applications.

No report can either be found in the literature showing a comparison between the concentrations of IGFBP-1 in amniotic fluid and other secretions present in vagina. A research group led by the inventor of the present invention has now studied the concentrations of IGFBP-1 in amniotic fluid and blood, as well as the concentrations in secretions that are possibly present in the vagina (Table 1).

TABLE 1

Concentrations of IGFBP-1, prolactin (PRL) and alpha-fetoprotein (AFP) in samples of maternal serum (S) and amniotic fluid (AF) are shown in the Table. The samples were taken at gestation of 24–38 weeks.

| Patient | Sample | IGFBP-1 (µg/l) | ratio | PRL (µg/l) | ratio | AFP (U/ml) | ratio |
|---|---|---|---|---|---|---|---|
| 1 | S | 170 | | 140 | | | |
|   | AF | 60000 | 353 | 1800 | 13 | | |
| 2 | S | 130 | | 76 | | | |
|   | AF | 29000 | 223 | 320 | 4 | | |
| 3 | S | 140 | | 83 | | | |
|   | AF | 48000 | 343 | 260 | 3 | | |
| 4 | S | 200 | | 118 | | | |
|   | AF | 65000 | 325 | 340 | 3 | | |
| 5 | S | 63 | | 183 | | | |
|   | AF | 22000 | 349 | 210 | 1 | | |
| 6 | S | 350 | | 124 | | | |
|   | AF | 350000 | 1000 | 300 | 2 | | |
| 7 | S | 240 | | 78 | | | |
|   | AF | 115000 | 479 | 420 | 5 | | |
| 8 | S | 190 | | 150 | | | |
|   | AF | 40000 | 210 | 350 | 2 | | |
| 9 | S | 240 | | 183 | | 75 | |
|   | AF | 50000 | 208 | 390 | 2 | 240 | 3 |
| 10 | S | 250 | | 62 | | 150 | |
|   | AF | 200000 | 800 | 583 | 9 | 333 | 2 |
| 11 | S | 130 | | 100 | | 162 | |
|   | AF | 70000 | 538 | 728 | 7 | 367 | 2 |
| 12 | S | 65 | | 60 | | 98 | |
|   | AF | 33000 | 508 | 400 | 7 | 139 | 1 |

TABLE 1-continued

Concentrations of IGFBP-1, prolactin (PRL) and alpha-fetoprotein (AFP) in samples of maternal serum (S) and amniotic fluid (AF) are shown in the Table. The samples were taken at gestation of 24–38 weeks.

| Patient | Sample | IGFBP-1 (μg/l) | ratio | PRL (μg/l) | ratio | AFP (U/ml) | ratio |
|---|---|---|---|---|---|---|---|
| 13 | S | 600 | | 190 | | 98 | |
| | AF | 70000 | 117 | 447 | 2 | 372 | 4 |
| 14 | S | 260 | | 69 | | 242 | |
| | AF | 95000 | 365 | 433 | 6 | 178 | 1 |
| 15 | S | 340 | | 130 | | 137 | |
| | AF | 180000 | 529 | 443 | 3 | 196 | 1 |
| 16 | S | 500 | | 94 | | 97 | |
| | AF | 155000 | 310 | 1173 | 12 | 377 | 4 |
| 17 | S | 155 | | 154 | | 233 | |
| | AF | 19000 | 122 | 46 | <1 | 214 | 1 |
| 18 | S | 340 | | 129 | | 47 | |
| | AF | 140000 | 412 | 573 | 4 | 229 | 5 |
| 19 | S | 160 | | 40 | | 153 | |
| | AF | 200000 | 1250 | 1301 | 33 | 1252 | 8 |
| 20 | S | 240 | | 104 | | 71 | |
| | AF | 160000 | 667 | 964 | 9 | 151 | 2 |
| 21 | S | 340 | | | | 201 | |
| | AF | 145000 | 426 | | | 111 | <1 |
| 22 | S | 350 | | 116 | | 181 | |
| | AF | 53000 | 151 | 194 | 2 | 246 | 1 |
| 23 | S | 200 | | 92 | | 55 | |
| | AF | 125000 | 625 | 191 | 2 | 121 | 2 |
| 24 | S | 135 | | 131 | | | |
| | AF | 55000 | 407 | 790 | 6 | | |
| 25 | S | 340 | | 35 | | | |
| | AF | 145000 | 426 | 248 | 7 | | |

It can be concluded from the paired blood and amniotic fluid samples studied that even though there are remarkable and individually varying amounts of IGFBP-1 in blood, the concentration of IGFBP-1 in amniotic fluid is in all cases more than 100 times higher than in maternal serum. The said difference in concentrations is the largest difference between a protein in blood and in amniotic fluid known to the inventor. For this reason, IGFBP-1 is well suited for detecting the presence of amniotic fluid also in situations where the amniotic fluid is mixed with blood.

Contrarily, the corresponding ratios of the proteins AFP and PRL vary considerably, being on the magnitude of 1–10. In some cases, even higher concentrations of the compounds to be measured were found in serum than in amniotic fluid. These measurements also show why the earlier tests based on the measurements of AFP and PRL have not been completely reliable.

According to the present invention, it was observed that by adjusting the detection limit of the IGFBP-1 test to such a level that even a high blood concentration of IGFBP-1 does not give a positive result, one can make sure that a positive result always derives from the presence of amniotic fluid. In this way, IGFBP-1 also from amniotic fluid in a low concentration can be detected even if there is only a very small amount of amniotic fluid mixed in the blood.

The detection limit can be adjusted to a suitable level, for instance by using a label that produces such a weak signal that a low concentration of IGFBP-1 caused by only blood or some other secretion in the sample will not give a result interpreted as positive. When using a strong signal, the detection limit can be lowered, e.g., by diluting the sample. If the signal used gives a quantitative result, it can be interpreted as negative when the concentration of IGFBP-1 in the sample is below the highest known concentration caused by maternal serum.

It has also been shown in studies that the concentration of IGFBP-1 in the vaginal secretions of non-pregnant women and pregnant women with intact membranes, in seminal plasma, or in urine is extremely low compared to that in amniotic fluid. Therefore, the test can be so designed that sources of IGFBP-1 other than amniotic fluid cannot cause false positive results under the test conditions used. As shown in Table 1, the highest concentration of IGFBP-1 found in the studies in maternal serum was 600 μg/l, while the lowest concentration in amniotic fluid was 22,000 μg/l. Consequently, even if the amniotic fluid content in the sample is as small as 10%, the IGFBP-1 concentration caused by the presence of amniotic fluid would still be 2200 μg/l, which is over three times more than the highest concentration measured in maternal serum. Most often, the IGFBP-1 concentration in amniotic fluid is considerably higher than that mentioned above (22000 μg/l) and correspondingly, the concentration in maternal serum is considerably lower than that mentioned above (600 μg/l).

A small amount (100–200 μl) of vaginal secretion is sufficient for performing the test. The sample is preferably taken during a speculum examination using, for example, a disposable syringe or a sterile instrument especially designed for this purpose.

Since the molecular size of IGFBP-1 is big enough, its molecular weight being about 25,000 D, it has been possible to raise antibodies against it, and these antibodies can be utilized in an immunological assay method.

Thus, the method according to the present invention is based on the use of antibodies against IGFPB-1 or other specific binding substances of IGFBP-1. It is rapid, and its working range covers a suitable range of concentrations, and consequently it is well suited for the diagnostic use which is the object of the present invention, i.e., to detect the rupture of fetal membranes by verifying the presence of amniotic fluid in the vagina.

It is now possible for the first time, by using the preferred assay method of IGFBP-1 according to the present invention, to detect amniotic fluid in the vagina with sufficient specificity, because concentrations as high as those necessary for the measuring range of the assay do not exist elsewhere than in amniotic fluid. Therefore there will not be any false positive results caused by contamination from another IGFBP-1 source.

In a preferred embodiment of the invention, the measuring range is so adjusted that IGFBP-1 derived from blood cannot cause a false positive result. Thus, the test is also so insensitive that the normally occurring minor leakage of amniotic fluid through intact fetal membranes cannot cause a false interpretation. As the binding substance or binding substances used in the test only bind IGFBP-1 specifically, the possibility of a positives reaction being caused by a so-called cross-reaction, i.e., the binding of the wrong compound, is also eliminated.

On the other hand, the concentration of IGFBP-1 in amniotic fluid is always so high that the fluid that leaks in connection with a rupture of fetal membranes cannot remain undetected in a test according to the invention. The test utilizes a specific binding substance that binds to IGFBP-1 with such a high affinity that in spite of its rapid performance time, the test 411 begin to turn positive starting from a desired IGFBP-1 concentration in the sample.

In developing the test, attention has also been paid to eliminating the so-called Hook effect (effect of the prozone phenomenon). This effect( means that in an immunological reaction, an antigen concentration that is very high compared to the antibody concentration may cause a spurious decrease of the antigen-antibody complexes to be measured. In this case, a sample with a high concentration may contrarily give a low result, which in a test of the present kind, would be extremely detrimental and would cause a false negative result. For this reason, when developing the preferred embodiment of the test method according to the present invention, the ratio of the amounts of the binding reagents and the IGFBP-1 to be measured has been adjusted so that even the highest known concentration in amniotic fluid cannot cause the signal measured to become negative, consequently causing an incorrect interpretation. In this way, the risk of a false negative result is essentially eliminated in the test according to the invention.

The IGFBP-1 test according to the present invention has been developed to give a result as rapidly as possible, which is both medically and economically important in establishing the diagnosis intended in the invention. The required sample can be taken, for instance, during a gynaecological speculum examination when the rupture of membranes is suspected. The sample can be taken, for example, into a syringe or with a sampling instrument made for this purpose.

According to a preferred embodiment of the invention, the ratio of the concentrations of the specific binding substances and of IGFBP-1 originating from the sample has been adjusted to be suitable in the method so that the signal leading to a positive interpretation will only occur when the IGFBP-1 concentrations in the sample are high. The correct ratio is achieved, for example, by diluting the secretion sample taken for the diagnosis before the test itself is performed. The dilution is performed with a solution that is favourable for the binding reaction taking place in the test, preferably with a solution belonging to the test. The solution is preferably a buffer such as, for instance, a phosphate buffer that contains protecting proteins and having a pH close to physiological.

In the tests performed in practice, it has been noted that the dilution should be at least 1:10 to obtain a reliable result and, advantageously, at least 1:20. Greater dilutions may also be used even up to 1:500 or even greater. In order to get a result according to the invention, a qualitative result, i.e., + or −, is sufficient wherefore the level of dilution is not critical, as long as it is above the threshold in which, for instance, the IGFBP-1 present in maternal blood could give a positive result in the measuring range of the chosen label.

The test can also be performed with an undiluted sample, for instance by using very large amounts of specific binding substance and a label, the signal of which is not very strong. Thus, only the high concentration of IGFBP-1 derived from the amniotic fluid can give a positive result.

According to the invention, the IGFBP-1 test is advantageously performed using two specific monoclonal antibodies, for instance, so that one antibody is attached to a small plastic bead and the other antibody is coupled to a label, like an enzyme, for instance horseradish peroxidase (HRP). The appropriately diluted sample, enzyme-labelled antibody and the antibody-coated bead in a gripper are placed in a test tube. When the mixture is incubated, the IGFBP-1 present in the sample will become attached on one hand to the bead and on the other hand to the labelled antibody. After incubation, the bead is removed from the tube and washed under running water. The bead is placed in a tube containing the substrate of the enzyme used as label. During incubation, a visually detectable colour develops if the sample contained a sufficient amount of IGFBP-1. The solution remains colourless if the sample did not contain IGFBP-1, or if its concentration was too low.

The IGFBP-1 test according to the invention can also be performed so that the first antibody is attached to the surface of a membrane developed for such test purposes. The sample is allowed to be in contact with the membrane, and the IGFBP-1 in the sample will bind specifically to said immobilized antibody. Then, a corresponding enzyme-coupled antibody is added, which in turn binds to the IGFBP-1 now present on the membrane. The bound enzyme is detected by adding to the washed membrane a precipitating substrate of the enzyme, which substrate will change its colour as a result of the action of the enzyme. Thus, when the sample is positive, a visually detectable colour develops on the membrane. This kind of test based on a membrane coated with antibody can be carried out, for instance, by attaching the membrane in question to a plastic vessel, which is especially designed for such a purpose. An absorbing material placed under the membrane will rapidly absorb the test liquids through the membrane, when said liquids are pipetted onto the membrane. Correspondingly, the membrane can be attached to a plastic strip, which is transferred from one solution to another.

A colour indicating a positive result can also be obtained otherwise than by labelling the antibody with an enzyme, which in turn causes the change in the colour of its substrate. Instead of an enzyme, a dye can be attached to the antibody. The intensity of the dye should be sufficiently strong, so that in the positive case, the colour of the label bound to the immobilized IGFBP-1 is visually detectable. Gold or selenium colloids or disperse dyes can be used as such dyes. The advantage of such dyes is that the perfomance of the test is shorter when a separate substrate reaction phase is not needed. Correspondingly, the antibody can be coupled to coloured latex particles. When such a detection based on a direct visual colour is used, an immunochromatographic rapid test method can be used for IGFBP-1. Typically, a membrane is used, wherein a first antibody is attached to a small area. To another area, a second colour-labelled antibody is dried. Said second antibody starts to migrate on the membrane when a liquid sample is added. If the sample contains a sufficient amount of IGFBP-1, a coloured zone will develop at the point where the antigen bound to the labelled antibody further binds to the antibody immobilized to the membrane. If the sample is negative, no coloured zone develops, and the dye migrates over the membrane.

The IGFBP-1 test can also be performed by the agglutination principle. Here, the visually detectable reaction comprises the agglutination of, for instance, antibody-oated particles, like latex, with the antigen in the sample causing bonds between them. Inversly, an inhibition of agglutination can also be detected.

Not only antibodies, but also other specific IGFBP-1 binding substances and their combinations can also be used in the method and test kits according to the present invention. In this way, for instance, the natural binding characteristic of IGFBP-1 to IGF (Insulin-like growth factor) can be exploited.

In the performance of the test one may also use the assay methods explained in FI-patent 84863, the contents of which are included herein by reference.

The methods for testing for IGFBP-1 according to the present invention can ease the problems related to the premature rupture of membranes in a decisive way. After the rupture of membranes, the patient needs an intensive follow-up until delivery because of the risk of infection. When a premature rupture of fetal membranes is suspected, one has to decide on the basis of an examination whether the patient should be admitted to the hospital or allowed to go home. This decision is important both economically and medically: economically, as costs of bed-days to society; and medically, because the decision directly influences the mortality of both foetus and mother.

The test kit according to the present invention contains a reagent that is based on a specific binding substance for IGFBP-1. Depending on the test method, the reagent may be a binding substance solution, a solid phase like a bead or a membrane coated with the specific binding substance, or it may be formed of latex or dye particles. For example, in a one-step assay, the kit may also contain a combination of the above mentioned components. The specific binding substance advantageously comprises a specific monoclonal antibody to IGFBP-1.

In addition to the reagent mentioned above, the kit advantageously contains a label that is able to detect a sufficient concentration of IGFBP-1 in the sample after the binding reaction. The label detecting the binding reaction is advantageously a signal producing label coupled to another antibody to IGFBP-1. The label is, for example, an enzyme coupled to another antibody to IGFBP-1, a radioactive isotope or a compound recognized by its colour. If the label is an enzyme, the test kit advantageously contains a substrate of the enzyme.

In addition to the essential reagents, it is advantageous that the test kit contains a dilution solution for diluting the sample. Said solution advantageously comprises an assay buffer, for instance phosphate buffer containing protective proteins and having a pH close to the physiological pH. The amount of dilution buffer may be adjusted so as to achieve a final dilution, for instance 1:20, when a certain amount of sample is added to it.

The test kit may also contain a sampling instrument such as a disposable sterile syringe or an instrument especially developed for the test.

The test kit may also consist of a simple instrument for taking a vaginal secretion sample and an associated dilution solution for performing the test. The test kit may also comprise an antibody-coated test strip that the patient herself can insert into the vagina. Such test kits are well suited to home tests that a woman can use herself at home when she suspects that the fetal membranes are ruptured and wonders whether she should go to the hospital or not.

The Examples below illustrate the performance of the test according to the invention without, however, limiting it in any way.

EXAMPLE 1

Plastic beads were coated with anti-IGFBP-1 antibody (6305, Medix Biochemica). Another IGFBP-1 antibody (6303, Medix Biochemica) was coupled with a label enzyme (horseradish peroxidase, HRP). Phosphate buffer containing 0.3% bovine serum albumin (BSA) was used as assay buffer. The buffer also contained a detergent and stabilizers, and its pH was 7.4. A rapid IGFBP-1-test was performed according to the following instructions.

The performance of the rapid IGFBP-1-test:

1. 200 µl of 6303-HRP-label were pipetted into the sample tube (diluted 1:50 in assay buffer).

2. 100 µl of sample (diluted 1:20 in assay buffer) were added to the tube.

3. An IGFBP-1-antibody coated be;ad in a gripper was placed into the tube. It was incubated for 5 minutes.

4. The bead in the gripper was removed from the solution and washed under running water for 30 seconds.

5. The washed bead was transferred to the substrate solution (2,2'-azino-di-[3-ethyl-benzthiazoline sulfonate (6)], ABTS) (400 µl pipetted in a clear tube).

6. The tube was allowed to stand protected from light in an amber shielding vial for 5 minutes.

7. The colour of the solution was either inspected immediately, or the reaction was stopped by adding stopping solution (200 µl) and inspected: a colourless solution was negative, green was positive.

In order to make a comparison and to verify the appropriate dilution, tests were performed according to the procedure described above in Example 1, where the sample was amniotic fluid, in which the IGFBP-1 concentration was about 200,000 µg/l and which was diluted 1:20, 1:100, 1:500 and 1:2500 before the test, and correspondingly, a serum sample, in which the IGFBP-1 concentration was>100 µg/l, and which was diluted 1:20 before the test.

Typical absorbances measured are presented below:

| Sample | Dilution | $A_{414}$ | Visual estimation |
| --- | --- | --- | --- |
| Amniotic fluid | 1:20 | 0.931 | + |
| Amniotic fluid | 1:100 | 1.021 | + |
| Amniotic fluid | 1:500 | 0.679 | + |
| Amniotic fluid | 1:2500 | 0.212 | ± |
| Serum 1. | 1:20 | 0.044 | − |
| Serum 2. | 1:20 | 0.049 | − |
| Assay buffer | 0 | 0.036 | − |

EXAMPLE 2

A narrow zone of a nitrocellulose strip is coated with an IGFBP-1-antibody (6305, Medix Biochemica). Coloured latex-particles are also coated with another IGFBP-1-antibody (6303, Medix Biochemica). The coated latex particles are dried on the other end of the membrane strip containing the zone of antibodies. The rapid IGFBP-1 test is performed on the membrane according to the following instructions.

Performance of the IGFBP-1 membrane test:

1. A few drops of a sample, diluted with buffer are pipetted on the part of the strip where the latex particles are dried.

2. During a few minutes' incubation, the sample migrates on the membrane and the latex particles are transferred with the liquid over the antibody-coated zone to the other end of the strip.

3. The strip is inspected. If a coloured zone is formed, the result is positive.

EXAMPLE 3

A small area of nylon membrane is coated with IGFBP-1-antibody (6305, Medix Biochemica). The coated membrane is placed on a plastic cup-like vessel so that directly underneath there is attached an absorbing material (treated cellulose). Another IGFBP-1-antibody (6303, Medix Biochemica) is coupled to a labeled enzyme (horseradish peroxidase, HRP). A rapid IGFBP-1 test is performed according to the following instructions.

1. A few drops of sample diluted with assay buffer are pipetted onto the membrane and the solution is allowed to absorb through the membrane.

2. As much wash solution as the cup will hold (about 1 ml) is pipetted and the solutions allowed to absorb through the membrane.

3. A few drops of the label solution are pipetted and the solution is allowed to absorb through the membrane.

4. Wash solution, about 1 ml, is pipetted and the solution is allowed to absorb through the membrane.

5. A few drops of a precipitating substrate of the enzyme are pipetted on the membrane and the solution is allowed to absorb through the membrane.

6. The membrane is inspected. If a coloured zone is formed, the result is positive.

The performance of the test according to the invention is illustrated above via some immunometric methods. However, it is evident to persons skilled in the art that the methods may be changed and varied within the above description and the appended claims without deviating from the s cope of the invention.

I claim:

1. A diagnostic method for detecting rupture of fetal membranes in a pregnant woman comprising:

obtaining a sample of vaginal secretions from the pregnant woman, reacting the sample with at least one binding substance that specifically binds to insulin-like growth factor binding protein 1, IGFBP-1, in order to detect a level of IGFBP-1 in the sample, and detecting a level of IGFBP-1 in the sample above a predetermined threshold level, the predetermined threshold level being selected as indicative of amniotic fluid in the vaginal secretion sample, wherein a level of IGFBP-1 in the sample above the predetermined threshold level is indicative of rupture of fetal membranes in the pregnant woman.

2. The method according to claim 1, wherein said at least one binding substance that specifically binds to IGFBP-1 is an antibody specific for IGFBP-1.

3. The method according to claim 2, wherein said antibody is a monoclonal antibody.

4. The method according to claim 3, wherein said monoclonal antibody is a member selected from the group consisting of monoclonal antibody 6303 and monoclonal antibody 6305.

5. The method according to claim 1, wherein the sample is reacted with a binding substance that specifically binds to IGFBP-1 and another, detectably-labelled, binding substance that specifically binds to IGFBP-1.

6. The method according to claim 5, wherein said binding substance that specifically binds to IGFBP-1 is a monoclonal antibody, and said another, detectably-labelled binding substance that specifically binds to IGFBP-1 is a monoclonal antibody coupled to a label.

7. The method according to claim 6, wherein said label is a member selected from the group consisting of an enzyme and a dye.

8. The method according to claim 1, wherein said vaginal secretion sample is diluted prior to said reacting stem in order to decrease the level of said IGFBP-1 in said sample.

9. The method according to claim 8, wherein said vaginal secretion sample is diluted fat least 1:10.

10. The method according to claim 8, wherein said vaginal secretion sample is diluted at least 1:20.

11. The method according to claim 1, wherein said at least one binding substance that specifically binds to IGFBP-1 is detectably-labelled and provides a detectable signal when the level of IGFBP-1 in the sample is above said threshold level.

* * * * *